US00PP34069P2

(12) United States Plant Patent
Sills et al.

(10) Patent No.: US PP34,069 P2
(45) Date of Patent: Mar. 29, 2022

(54) BLACKBERRY PLANT NAMED 'DRISBLACKTWENTYFIVE'

(50) Latin Name: ***Rubus* L. subgenus *Rubus***
Varietal Denomination: DrisBlackTwentyFive

(71) Applicant: Driscoll's, Inc., Watsonville, CA (US)

(72) Inventors: Gavin R. Sills, Watsonville, CA (US); Yunwen Wang, Watsonville, CA (US); Mark F. Crusha, Watsonville, CA (US); John Fangary, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/085,997

(22) Filed: Oct. 30, 2020

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
CPC ... A01H 5/08; A01H 5/00; A01H 6/74; A01H 6/7499
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| PP31,110 | P2 | 11/2019 | Sills et al. |
| PP31,291 | P2 | 12/2019 | Sills et al. |
| PP31,825 | P2 | 6/2020 | Sills et al. |
| PP31,826 | P2 | 6/2020 | Sills et al. |
| PP32,268 | P2 | 10/2020 | Sills et al. |
| 2016/0249505 | P1 | 8/2016 | Sills et al. |

OTHER PUBLICATIONS

Sills et al., "Unpublished U.S. Appl. No. 16/602,974, filed Jan. 8, 2020, titled Blackberry Plant Variety Named Drisblacktwentyfour".
Sills et al., "Unpublished U.S. Appl. No. 16/602,975, filed Jan. 8, 2020, titled Blackberry Plant Variety Named Drisblacktwentythree".
Sills et al., "Unpublished U.S. Appl. No. 16/602,976, filed Jan. 8, 2020, titled Blackberry Plant Variety Named Drisblacktwentytwo".
Voss, Donald H. "The Royal Horticultural Society Colour Chart 2001", Journal American Rhododendron Society, vol. 56, No. 1,2002, 3 pages.
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — June Hwu
(74) *Attorney, Agent, or Firm* — Morrison & Foerster LLP

(57) ABSTRACT

A new and distinct variety of blackberry plant named 'DrisBlackTwentyFive', selected for its yield, fruit size, firmness, and flavor, as well as fruiting on primocanes, is disclosed.

5 Drawing Sheets

Latin name:
Botanical classification: *Rubus* L. subgenus *Rubus*.
Varietal denomination: The varietal denomination of the claimed variety of blackberry plant is 'DrisBlackTwenty-Five'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackTwentyFive'.

Blackberry plant variety 'DrisBlackTwentyFive' was discovered in Santa Cruz, Calif. in July of 2012 and originated from a cross between the female parent blackberry plant 'BQ9417' (unpatented) and the male parent blackberry plant 'DrisBlackTwelve' (U.S. Plant Pat. No. 27,746). The original seedling of the new variety was first asexually propagated via root cuttings in Santa Cruz, Calif. in October of 2012.

'DrisBlackTwentyFive' was subsequently asexually propagated via root cuttings, and underwent testing in Santa Cruz, Calif. from 2014 to 2019 (five years). The present variety has been found to be stable and reproduce true to type through successive asexual propagations via root cuttings and tissue culture.

'DrisBlackTwentyFive' was selected for its yield, fruit size, firmness, and flavor, as well as fruiting on primocanes.

BRIEF DESCRIPTION OF THE DRAWINGS

This new blackberry plant is illustrated by the accompanying photographs. The colors shown are as true as can be reasonably obtained by conventional photographic procedures. The photographs are of plants that are two to five years old.

DETAILED BOTANICAL DESCRIPTION

Figure 1:
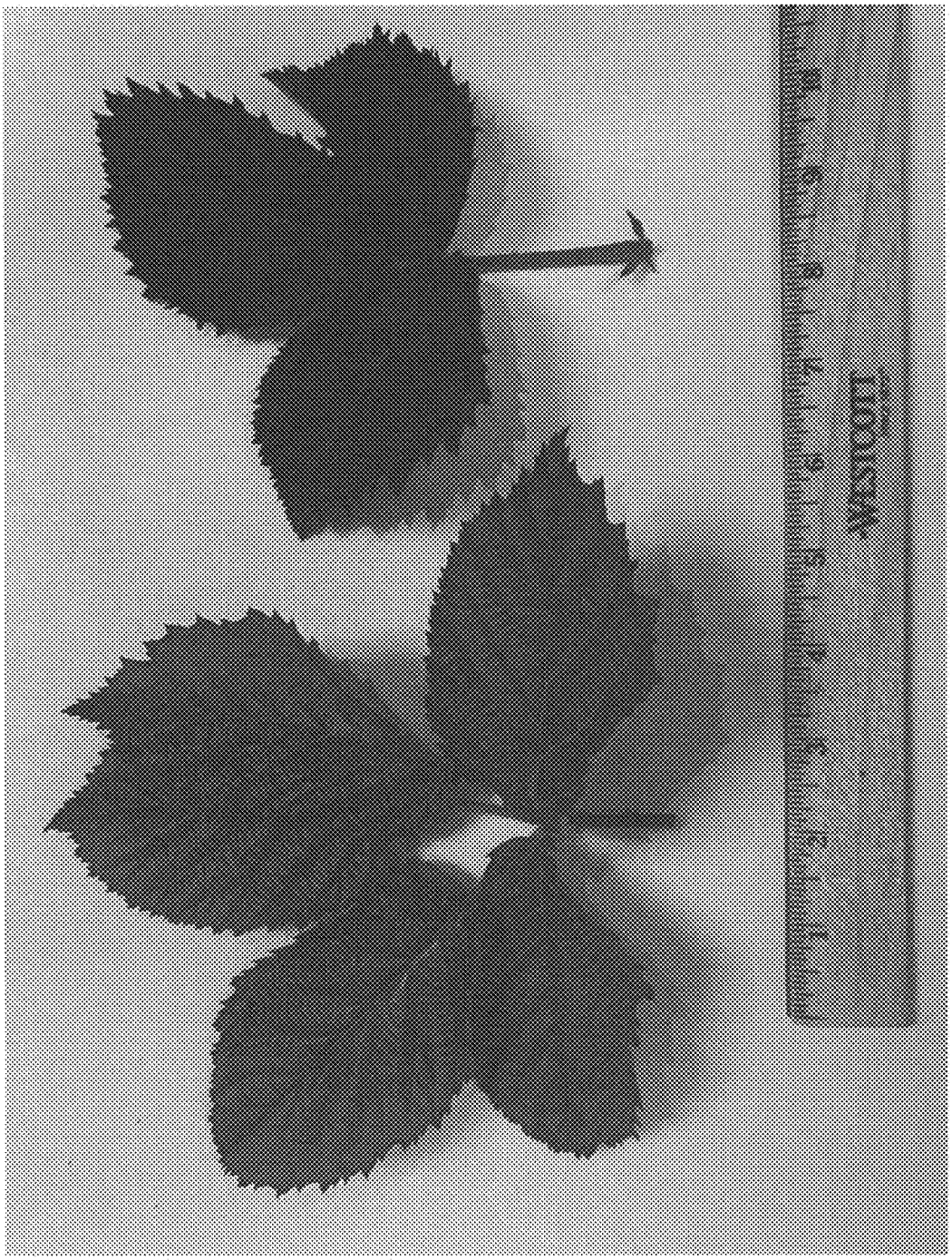
FIG. 1 illustrates leaves of variety 'DrisBlackTwentyFive'.
Figure 2:
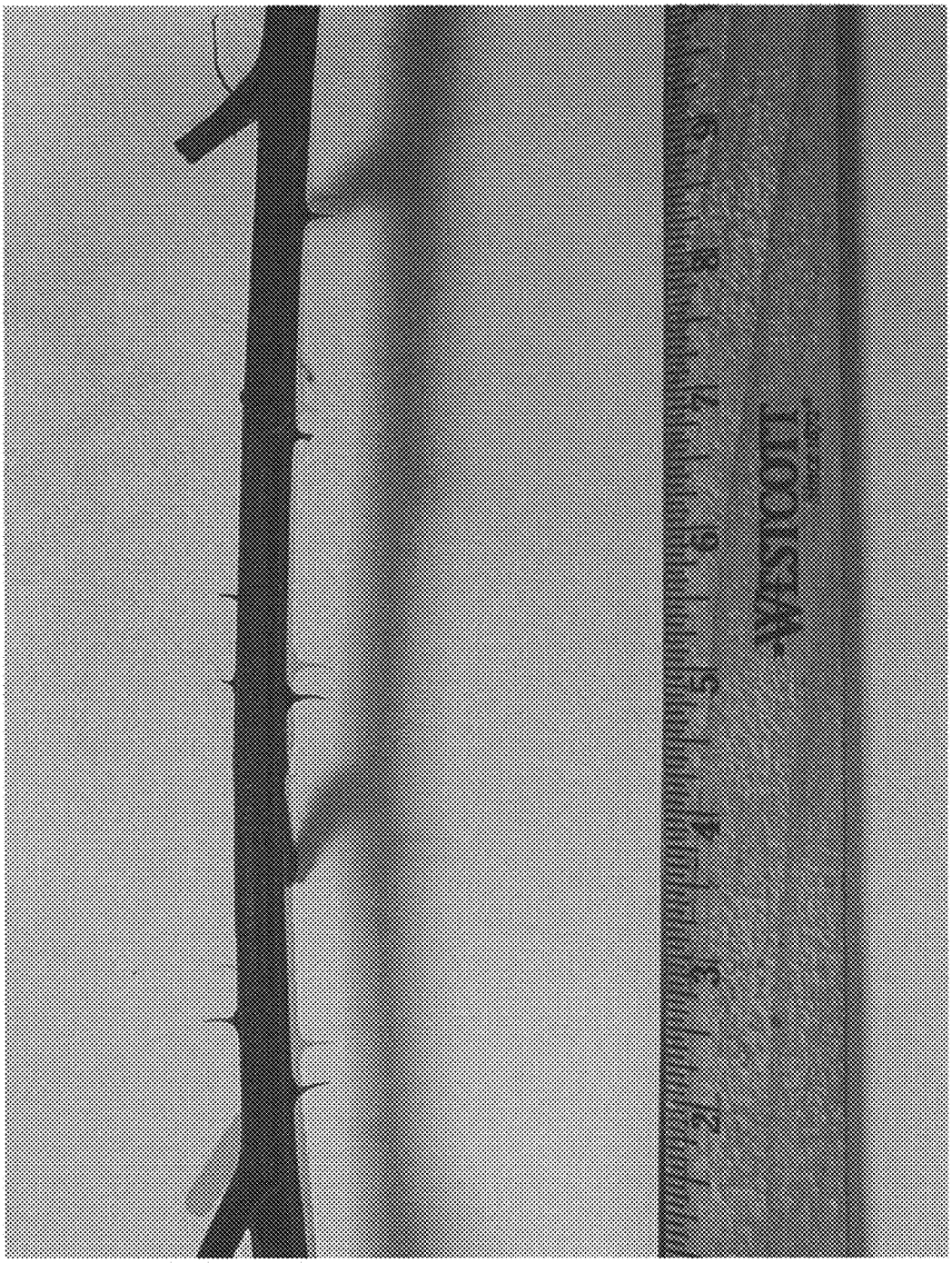
FIG. 2 illustrates a section of a cane of variety 'DrisBlackTwentyFive'.
Figure 3:
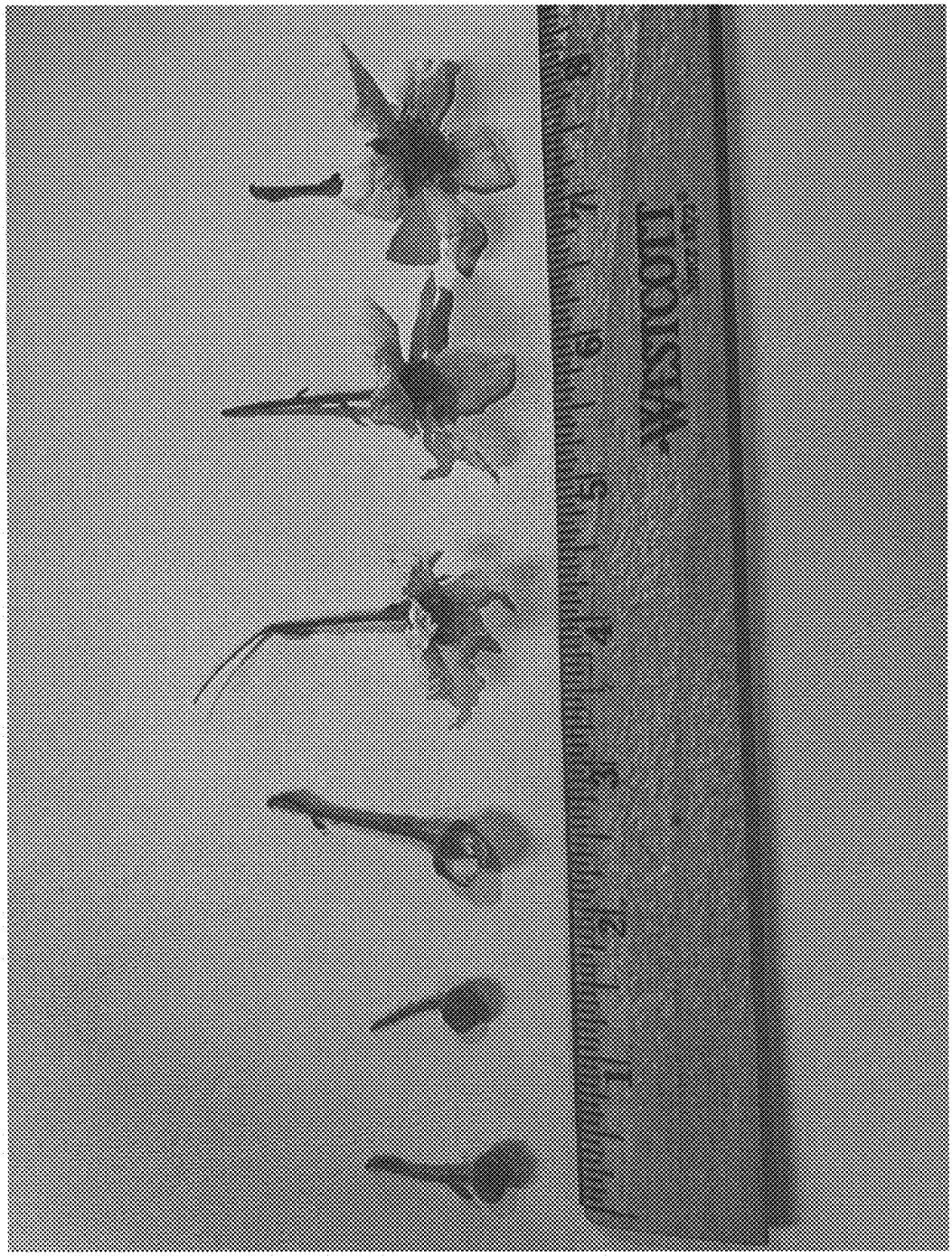
FIG. 3 illustrates flowers of variety 'DrisBlackTwentyFive' at various stages of development.
Figure 4:
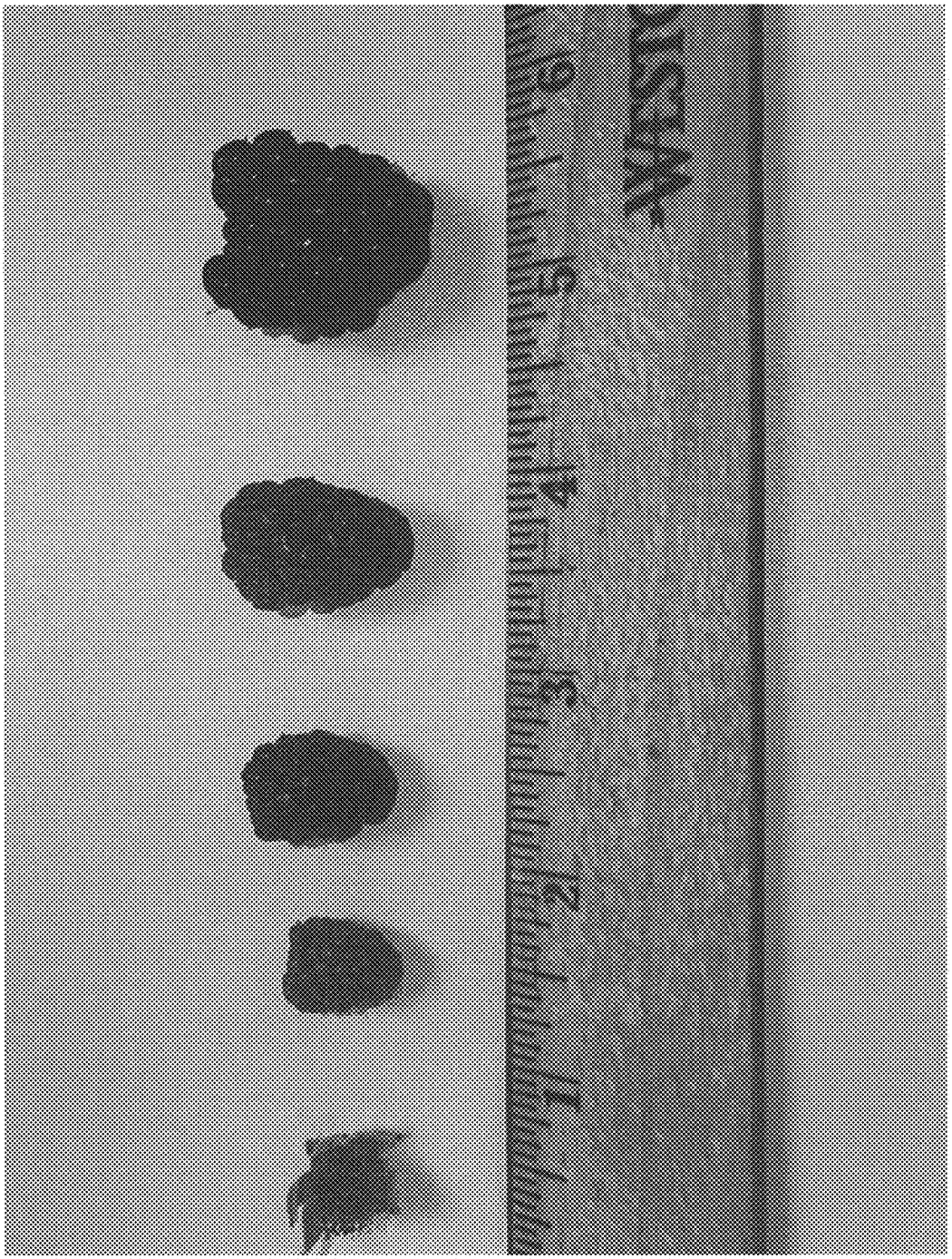
FIG. 4 illustrates fruits of variety 'DrisBlackTwentyFive' at various stages of development.
Figure 5:
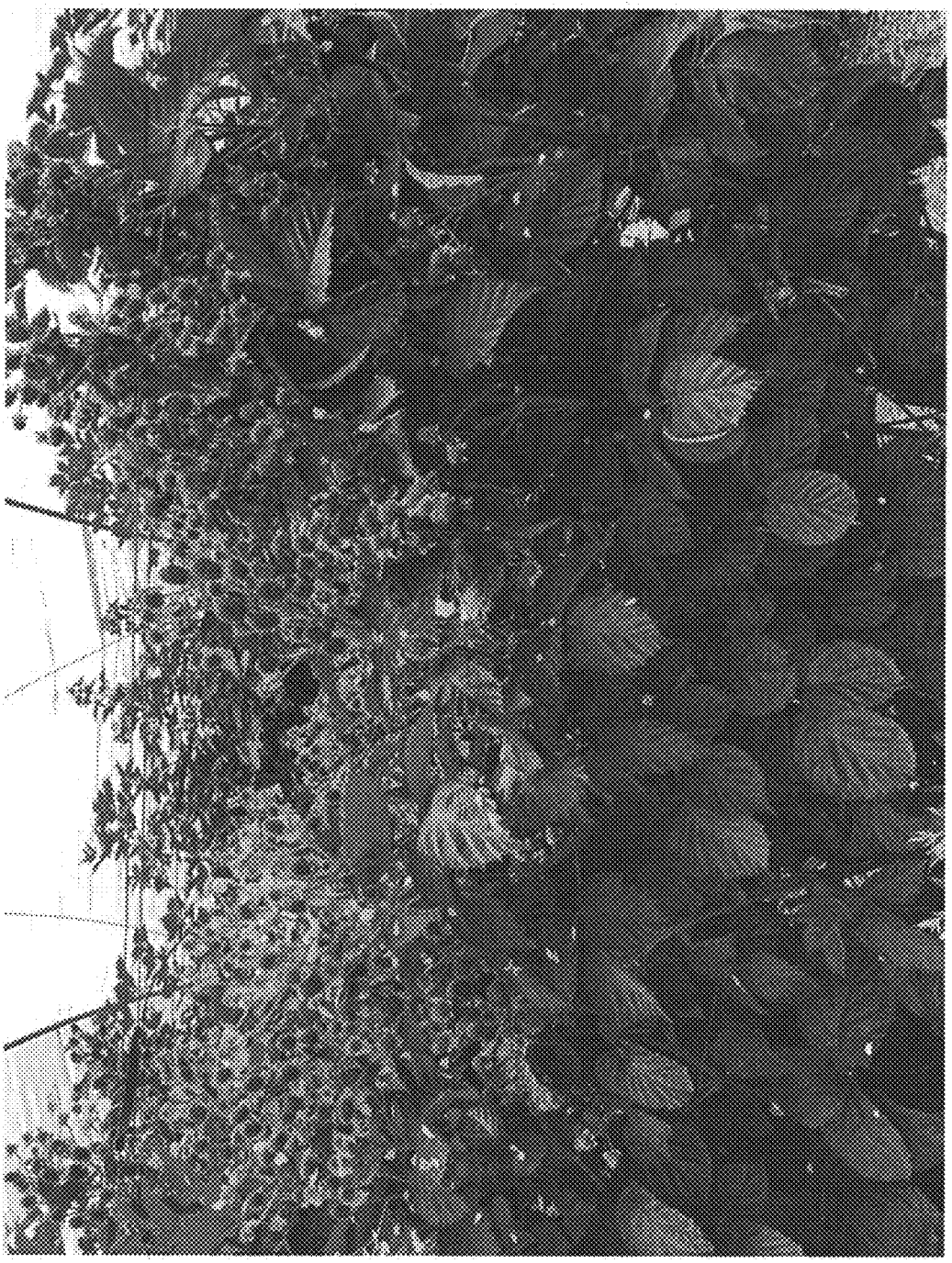
FIG. 5 illustrates a plant of variety 'DrisBlackTwentyFive'.

The following descriptions set forth the distinctive characteristics of 'DrisBlackTwentyFive'. The data that define these characteristics are based on observations taken in Santa Cruz, Calif. from 2014 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwentyFive' has not been observed under all possible environmental conditions. The botanical description of 'DrisBlackTwentyFive' was taken from plants that were two to five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family.*—Rosaceae.

*Botanical.*—*Rubus* L. subgenus *Rubus.*

*Common name.*—Blackberry.

*Variety name.*—'DrisBlackTwentyFive'.

Parentage:

*Female parent.*—'BQ942.7' (unpatented).

*Male parent.*—'DrisBlackTwelve' (U.S. Plant Pat. No. 27,746).

Plant:

*Propagation.*—Root cuttings and tissue culture.

*Growth habit.*—Upright.

*Height.*—242 cm.

*Width.*—69 cm.

*Height/width ratio.*—3.5.

*Vigor.*—Medium.

*Self-fruitfulness.*—Self-fruitful.

Canes:

*Internodal distance.*—9 cm.

*New cane.*—Number of new canes: Medium. Strength: Medium. Glaucosity (waxy bloom): Medium.

*Dormant cane.*—Anthocyanin coloration: Weak; RHS 176B (Moderate reddish brown). Predominant distribution of branches: Only on upper third. Cross-section: Angular to grooved. Dormant cane length: 242 cm. Spine: Presence of spines: Present. Number of spines on dormant cane: Medium. Length: 4 mm. Width: 1 mm. Color: RHS 142A (Strong yellow green). Texture: Medium hardness. Attitude of spine apex in relation to cane: Outwards. Density of spines on central third of cane: Medium.

*Fruiting lateral.*—Fruiting lateral length ($4^{th}$ lateral from tip): 38.1 cm. Number of fruits per fruiting lateral: 22.

*Young shoots.*—Length: 73 cm. Diameter: 1 cm. Intensity of green color: Medium; RHS 139D (Moderate yellow green). Number of glandular hairs: Medium. Time of young shoot emergence: Mid-March.

Leaves:

*Time of leaf bud burst*.—Mid-March.

*Leaf*.—Predominant number of leaflets: 5. Type: Palmate. Relative position of lateral leaflets: Overlapping. Arrangement: Alternate. Venation: Cross-venulate. Vein color: RHS 135D (Light yellowish green). Intensity of green color of upper side: Medium, RHS 135A (Dark green). Intensity of green color of under side: Medium, RHS 135C (Strong yellowish green). Profile in cross-section: Flat (level with the leaflet blade). Glossiness of upper side: Weak.

*Leaflet*.—Texture of upper surface: Waxy with ridges, leathery to touch. Texture of lower surface: Soft with minor pubescence. Type of incision of margin: Biserrate. Depth of margin incisions: Medium.

*Terminal leaflet*.—Length: 10 cm. Width: 10 cm. Length/width ratio: 1. Shape: Ovate. Apex: Truncate. Base: Obtuse. Margin: Doubly serrate. Lobing: Absent. Shape in cross-section: U-shaped. Undulation of margin: Weak. Blistering between veins: Weak.

*Lateral leaflet* (*single leaflet in basal pair*).—Length: 10 cm. Width: 7 cm. Length/width ratio: 1.37. Shape: Ovate. Apex: Truncate. Base: Obtuse. Margin: Doubly serrate.

*Rachis* (*length between terminal leaflet and adjacent lateral leaflets*).—2 cm.

*Rachis color*.—RHS 138A (Moderate yellowish green).

*Petiole*.—Length: 4 cm. Diameter: 3 mm. Pigmentation of upper surface: Medium, RHS 143B (Strong yellow green). Pigmentation of under surface: Medium, RHS 143B (Strong yellow green). Petiole surface texture: Fuzzy with pubescence.

*Stipule*.—Length: 1 cm. Width: 2 mm. Color: RHS 143A (Strong yellow green). Orientation: Erect.

Inflorescence:

*Flower bud*.—Length: 3 mm. Width: 4 mm. Color: RHS 138B (Moderate yellow green).

*Flower*.—Diameter: 31 mm. Number of flowers observed at 3$^{rd}$ node from tip of lateral: 6. Fragrance: Very faint or absent.

*Petal*.—Length: 13 mm. Width: 10 mm. Length/width ratio: 1.3. Number of petals per flower: 5. Color: RHS 155B (Yellowish white). Shape: Ovate. Apex: Rounded. Base: Obtuse. Margin: Entire.

*Sepal*.—Length: 5 mm. Width: 4 mm. Color: RHS 138B (Moderate yellow green).

*Flower pedicel*.—Length: 19 mm. Diameter: 2 mm. Color: RHS 138A (Moderate yellowish green). Pedicel surface texture: Fuzzy with pubescence.

*Inflorescence peduncle*.—Length: 18 mm. Diameter: 2 mm. Color: RHS 138B (Moderate yellow green). Peduncle surface texture: Fuzzy with pubescence.

*Reproductive organs*.—Style: Length: 3 mm. Color: RHS 143B (Strong yellow green). Ovary: Color: RHS 143A (Strong yellow green). Pistil: Number of pistils per flower: 96. Stamen: Length: 2 mm. Color: RHS 145C (Light yellow green). Number of stamens per flower: 100. Pollen: Amount: Medium. Color: RHS 154D (Light yellow green).

*Time of beginning of flowering on previous year's cane* (*floricane*).—Early-March, flowering continuing to mid-April.

*Time of beginning of flowering on current year's cane* (*primocane*).—Mid-April.

Fruit:

*Length of mature fruit*.—28 mm.

*Diameter of mature fruit*.—20 mm.

*Ratio of length to width*.—1.4.

*Primocane fruit weight*.—7 g/fruit.

*Floricane fruit weight*.—8 g/fruit.

*Sweetness/soluble solids* (*in °Brix*).—11.

*Titratable acidity* (*% as citric acid*).—0.78%.

*Glossiness*.—Medium.

*Firmness*.—Medium.

*Fruit shape in longitudinal section*.—Medium ovate.

*Fruit color*.—RHS 203A (Black).

*Fruit flavor*.—Sweet.

*Drupe*.—Length of single drupe: 5 mm. Diameter of single drupe: 4 mm. Average number of drupes per fruit: 96.

*Seed*.—Diameter: 2 mm. Weight: 0.00258 g. Color: RHS 167D (Moderate orange yellow).

*Fruiting on current year's cane*.—Present.

*Harvest interval on current year's cane*.—Mid-August to early September.

*Harvest interval on previous year's cane*.—Mid-May to June.

*Yield*.—12,500 to 14,100 pounds (lbs) of fruit per acre per season from 24-36 month-old plants when grown in Watsonville, Calif.

*Market use of fruit*.—Fresh market.

*Shipping and storage characteristics*.—Following harvest, fruit can be stored for 12 days if maintained under cooled temperatures that are standard for blackberry storage.

Resistance to pests and diseases:

*Redberry mite* (*acalitus essigi*).—Moderately resistant.

*Fusarium wilt* (*fusarium oxysporum*).—Moderately resistant.

*Cold resistance*.—Hardy to USDA Hardiness Zone 9b, 25° F. to 30° F.

*Heat resistance*.—Moderately tolerant.

COMPARISONS TO PARENTAL AND REFERENCE BLACKBERRY VARIETIES

'DrisBlackTwentyFive' differs from the female parent 'BQ942.7' in that 'DrisBlackTwentyFive' has a larger fruit size and a higher yield potential as compared to 'BQ942.7'.

'DrisBlackTwentyFive' differs from the male parent and reference variety 'DrisBlackTwelve' (U.S. Plant Pat. No. 27,746) in that 'DrisBlackTwentyFive' has an angular to grooved cross-section of dormant cane, spines present on dormant cane, a flat (level with the leaflet blade) cross-section profile of leaf, and an erect orientation of stipule, whereas 'DrisBlackTwelve' has a rounded to angular cross-section of dormant cane, spines absent on dormant cane, a convex (margins rolled backwards) cross-section profile of leaf, and an clasping orientation of stipule. 'DrisBlackTwentyFive' also has higher vigor when compared to 'DrisBlackTwelve'.

'DrisBlackTwentyFive' differs from the reference variety 'DrisBlackThirteen' (U.S. Plant Pat. No. 27,681) in that 'DrisBlackTwentyFive' has an upright growth habit, the predominant distribution of branches on the dormant cane is only on the upper third, spines are present on dormant cane, and terminal leaflets have a u-shape in cross-section, whereas for 'DrisBlackThirteen' the growth habit is semi-upright, the predominant distribution of branches on dormant cane is over the whole length, spines are absent on dormant cane, and terminal leaflets have a v-shape in cross-section.

What is claimed is:

1. A new and distinct variety of blackberry plant designated 'DrisBlackTwentyFive' as shown and described herein.

* * * * *